United States Patent
Konno et al.

(10) Patent No.: US 8,158,755 B2
(45) Date of Patent: Apr. 17, 2012

(54) PRODUCTION METHOD OF GELATIN PARTICLES

(75) Inventors: Eriko Konno, Ibaraki (JP); Tatsumi Ishikawa, Ibaraki (JP); Tsuyoshi Kasahara, Ibaraki (JP)

(73) Assignee: Nitto Denko Corporation, Osaka (JP)

( * ) Notice: Subject to any disclaimer, the term of this patent is extended or adjusted under 35 U.S.C. 154(b) by 333 days.

(21) Appl. No.: 12/585,834

(22) Filed: Sep. 25, 2009

(65) Prior Publication Data

US 2010/0081790 A1    Apr. 1, 2010

(30) Foreign Application Priority Data

Sep. 25, 2008 (JP) .................................. 2008-246417

(51) Int. Cl.
*C07K 1/02* (2006.01)

(52) U.S. Cl. ........................................ 530/355; 530/354
(58) Field of Classification Search .................. 530/354, 530/355

See application file for complete search history.

(56) References Cited

FOREIGN PATENT DOCUMENTS

| JP | 1-17376 | 3/1989 |
|---|---|---|
| JP | 3879018 | 11/2006 |

*Primary Examiner* — Chih-Min Kam
(74) *Attorney, Agent, or Firm* — Wenderoth, Lind & Ponack, L.L.P.

(57) ABSTRACT

A method of producing gelatin particles, including immersing a discharge spout in a hydrophobic solvent, discharging an aqueous gelatin solution from a nozzle tip into the hydrophobic solvent, and lifting, after discharging, the nozzle from the hydrophobic solvent, which can produce particles having an object particle size in a high yield, and can produce gelatin particles that do not essentially require a classification operation.

16 Claims, 7 Drawing Sheets

16 — 13
12

14

15

PRODUCTION METHOD OF GELATIN PARTICLES

TECHNICAL FIELD

The present invention relates to a production method of gelatin particles used for embolization in embolic therapy of liver cancer, kidney cancer, spleen cancer, fibroid and the like, hemostasis of arteriorrahagia, treatment of embolic disease before surgery, and the like, which is capable of controlling the particle size with a simple apparatus and a simple means and suitable for high yield production.

BACKGROUND OF THE INVENTION

A transarterial embolization treatment has been currently employed for the treatment of liver cancer, fibroid, kidney cancer and the like. The treatment method is based on the mechanism in which an anti-cancer agent is injected into a cancer (myoma) tissue using a microcatheter, the blood vessels reaching the cancer (myoma) tissue are blocked with an embolic material while using a non-ionic contrast agent, whereby supply of nutrition to the cancer (myoma) is shut off to cause necrosis of the cancer (myoma). This treatment method is a tissue-selective treatment method which can minimize the side effects of necrosis of normal cells. With the recent progress of the medical technique, there is a demand for embolic materials having a particle size ranging from as small as 40 μm to as large as 2000 μm, which have a uniform particle size and a uniform shape, so that the blood vessels can be embolized at positions as close as possible to the target site to avoid an adverse influence on the healthy part, and a material suitable for the size of the blood vessels can be selected.

JP-B-3879018 discloses a production method of particles by a dispersion in liquid method. To be precise, a biocompatible substance is dissolved in a good solvent and the solution is added to a poor solvent for the biocompatible substance and stirred to give an emulsion. Then, the obtained emulsion is cooled to a temperature not higher than the gelling temperature of the biocompatible substance to form gel particles. The particles of the biocompatible substance are obtained from the thus-obtained gel particles. In addition, JP-B-1-17376 describes a production method of spherical gelatin particles by a dispensing in liquid method. To be precise, a nozzle is immersed in a hydrophobic solvent, the nozzle opening is reciprocated in the horizontal direction (pendular motion), and a gelatin solution is press-discharged from the nozzle tube into the hydrophobic solvent at a temperature not lower than the gelling temperature.

As a method of producing gelatin particles, the conventionally-employed dispersion in liquid method is shown in FIG. 1. According to the dispersion in liquid method, an aqueous gelatin solution 11 is fed into a hydrophobic solvent bath (hereinafter solvent bath) 16 containing a hydrophobic solvent 12 such as oil and the like (FIG. 1A), and the mixture is stirred or dispersed with an agitating blade 13 to give an aqueous gelatin solution droplet 14 (FIG. 1B), then the solvent bath 16 is cooled with cold water 15 and the like (FIG. 1C). While the dispersion in liquid method is convenient, since the particle size distribution of the obtained particles is very wide, from about a few μm to about a few thousand μm, the yield of gelatin particles having desired particle sizes becomes considerably low. What is more, complete classification is not available due to coagulation of substances even after a classification operation and the like. Thus, the method is not suitable for the production of microparticles such as granules and the like.

On the other hand, the dispensing in liquid method described in JP-B-1-17376 improves the problem in conventional dispensing in liquid method which requires a cutting means of gelatin solution in a hydrophobic solvent. However, in the method described in patent document 2 including horizontal movement of a nozzle, the droplets discharged from the nozzle are not easily detached therefrom, and the method was insufficient to stably produce 40-2000 μm gelatin particles.

SUMMARY OF THE INVENTION

The present invention has been made in view of such situation and aims to provide a production method of gelatin particles, which is capable of producing particles having a desired fine particle size in a high yield, and which does not require a classification operation.

Accordingly, the present invention provides the following.
(1) A method of producing gelatin particles, comprising immersing a discharge spout on a nozzle tip of a dispenser in a hydrophobic solvent, discharging a predetermined amount of an aqueous gelatin solution from said discharge spout into the hydrophobic solvent, lifting, subsequent to discharging, the discharge spout from the hydrophobic solvent, dehydrating water in the droplets of the aqueous gelatin solution formed in the hydrophobic solvent using a dehydrating solvent, washing the dehydrated gelatin particles with a poor solvent of the gelatin particles, drying the collected gelatin particles, and thermally crosslinking the dried gelatin particles, wherein the droplets of the aqueous gelatin solution formed at the discharge spout during discharging are disengaged from the discharge spout during lifting.
(2) The production method of the above-mentioned (1), wherein the discharging step comprises discharging an aqueous gelatin solution contained in a dispensing body from the discharge spout into the hydrophobic solvent by air pressure, and the particle size of the gelatin particles can be controlled by air pressure, piston-needle displacement, discharge time, or diameter of the nozzle discharge spout.
(3) The production method of the above-mentioned (1), wherein the discharge spout is immersed by 0.2 mm-3 mm in the hydrophobic solvent in the discharging step.
(4) The production method of the above-mentioned (1), wherein, in the discharging step, the vertical amplitude of the nozzle motion is 1-5 mm and the number of up-and-down motion is 1000 cycles or below per minute.
(5) The production method of the above-mentioned (1), wherein the hydrophobic solvent is stirred.
(6) The production method of the above-mentioned (1), wherein, in the discharging step, the aqueous gelatin solution is discharged from the discharge spout into the hydrophobic solvent with a pressure of not less than 0.001 MPa.
(7) The production method of the above-mentioned (1), wherein the concentration of the aqueous gelatin solution is 2 wt %-20 wt %.
(8) The production method of the above-mentioned (1), wherein the discharging step is performed using a container in which the aqueous gelatin solution is prepared, a piping for transporting the aqueous gelatin solution from the container to the dispensing body, a dispenser with a nozzle for discharging the aqueous gelatin solution into the hydrophobic solvent, and a bath for storing the hydrophobic solvent, and each apparatus can be temperature-controlled to maintain the temperature of the aqueous gelatin solution.

(9) The production method of the above-mentioned (1), wherein the hydrophobic solvent is at least one kind selected from the group consisting of animal oil, vegetable oil, mineral oil, silicone oil, fatty acid, fatty acid ester and an organic solvent.

(10) The production method of the above-mentioned (1), wherein the dehydrating solvent and the washing solvent are each at least one kind selected from the group consisting of acetone, isopropyl alcohol, ethanol, methanol, toluene, ethyl acetate, hexane and an organic halogen solvent.

(11) The production method of the above-mentioned (1), wherein the gelatin particles are washed by at least one method selected from the group consisting of sieving and centrifugation.

(12) The production method of the above-mentioned (1), wherein the dehydrated gelatin particles are dried by at least one method selected from the group consisting of ventilation drying, drying under reduced pressure and freeze-drying.

(13) The production method of the above-mentioned (1), wherein, in the thermal crosslinking step, the heating temperature is 80° C.-250° C., and the heating time is 0.5 hr-120 hr.

(14) The production method of the above-mentioned (1), wherein the gelatin particles have a spherical shape.

(15) The production method of the above-mentioned (1), wherein the gelatin particles after thermal crosslinking have a particle size of not more than 2000 μm.

(16) The production method of the above-mentioned (1), wherein, in the discharging step, the tip of the nozzle is heated to 20° C. or above, and the hydrophobic solvent is controllable to 0° C.-60° C.

(17) The production method of the above-mentioned (1), wherein a plurality of droplets of the aqueous gelatin solution are produced by alternately repeating the discharging step and the lifting step plural times.

According to the present invention, a production method is provided which can easily produce a material having any particle size in a high yield using a dispenser. Particularly, 40 μm-2000 μm gelatin particles can be produced stably.

DESCRIPTION OF THE INVENTION

Figure 1A:
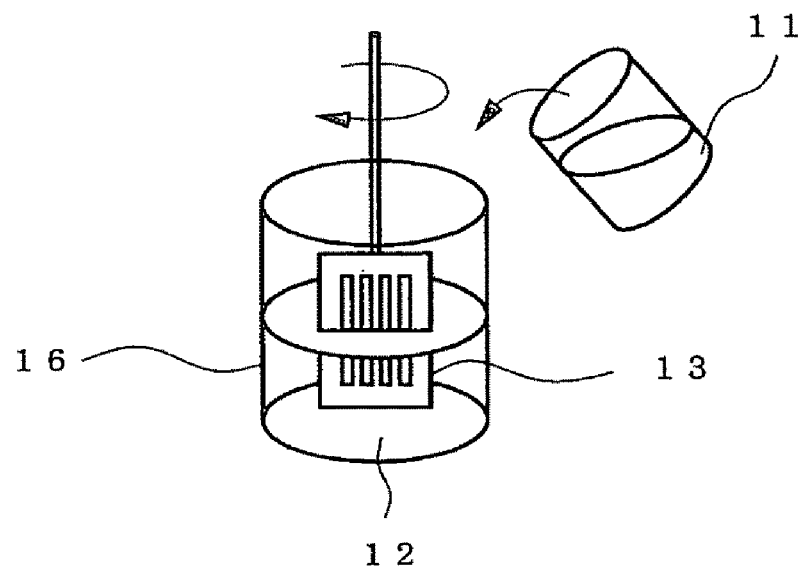
FIGS. 1A-1C are perspective views explaining a conventional dispersion in liquid method.
Figure 1B:
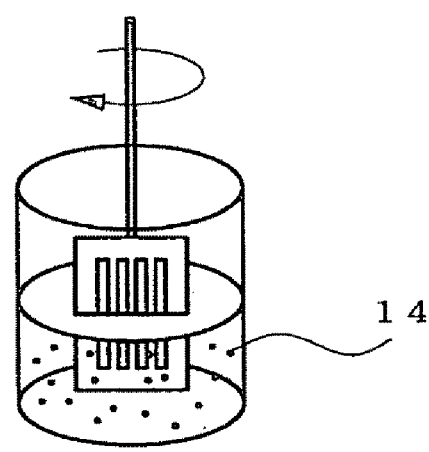
Figure 1C:
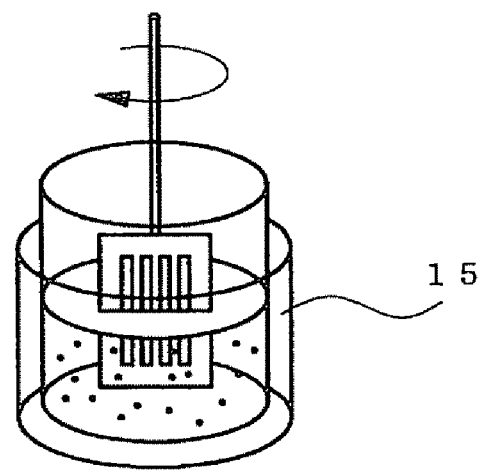

One embodiment of the present invention is explained in detail in the following by referring to drawings, wherein the explanation is simplified by according like symbols to the same elements as in FIG. 1.

Figure 2:
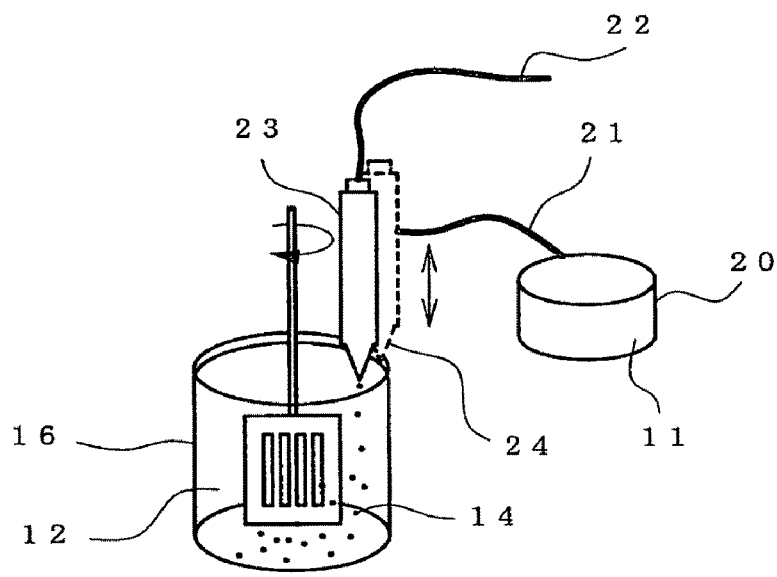
FIG. 2 is a perspective view explaining the dispensing in liquid method of one embodiment of the present invention.
Figure 3A:
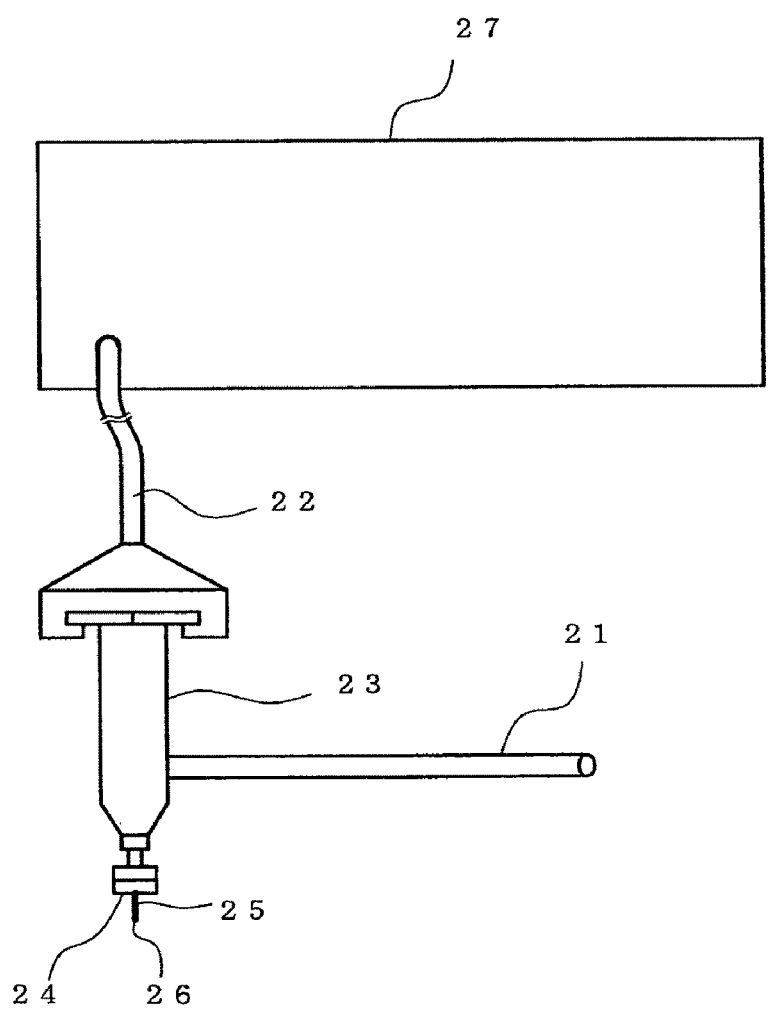
FIG. 3A shows the constitution of a dispenser.
Figure 3B:
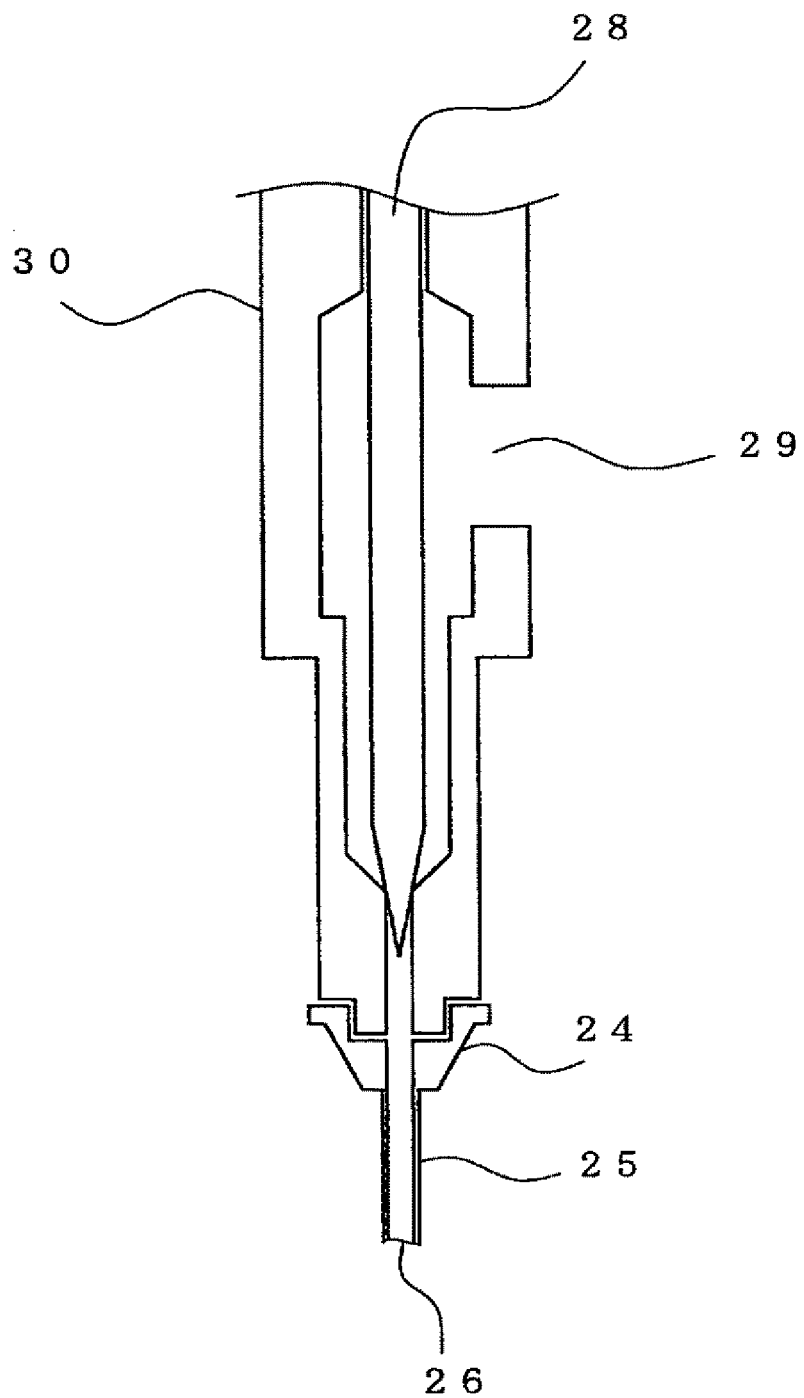
FIG. 3B is a sectional view of a dispenser tip.

As shown in FIG. 2 and FIGS. 3A, 3B, an aqueous gelatin solution 11 in an aqueous gelatin solution preparation container 20 is sent to a dispensing body 23 through a piping 21. A pressurized air 22 is connected to the body 23. The aqueous gelatin solution 11 in the body 23 is pressurized by the pressurized air 22 connected to a dispenser controller 27, and discharged from a discharge spout 26 on a needle 25 of a nozzle tip 24 connected to a liquid discharge mechanism 30 at a lower part of the body 23, into a hydrophobic solvent 12 contained in a solvent bath 16. What is important during discharging is that the aqueous gelatin solution be discharged into the hydrophobic solvent 12 when the discharge spout 26 is immersed in the hydrophobic solvent 12, and then the nozzle 24 be moved up such that the discharge spout 26 gets out from the hydrophobic solvent 12 and then moved down into the hydrophobic solvent 12 to repeat the series of operation. In FIGS. 3A, 3B, a needle nozzle suitable for dispensing a small amount is used for explanation, for example, a polypropylene needle nozzle (GP needle nozzles 30G, 32G, manufactured by SAN-EI TECH Ltd.). However, the shape of the nozzle is not limited to a needle nozzle.

As mentioned above, the aqueous gelatin solution 11 is discharged when the discharge spout 26 is immersed in the hydrophobic solvent 12, then the nozzle 24 is lifted so that the discharge spout 26 will be pulled out from the hydrophobic solvent 12, whereby the discharged aqueous gelatin solution 11 can be disengaged from the needle 25. In addition, since the discharge spout 26 is always immersed in the hydrophobic solvent 12 during discharge of the aqueous gelatin solution, the impact of drip of discharged aqueous gelatin solution droplets 14 on the surface of the hydrophobic solvent 12 can be eliminated. As a result, deformation of gelatin particles, and formation of fine particles resulting from splash of burst droplets can be suppressed. To afford the above-mentioned effects, the discharge spout 26 is desirably immersed in the depth of 0.5-3 mm in the hydrophobic solvent 12. When the depth is less than 0.5 mm, the immersion state may not be ensured. Although the immersion depth may be larger, vertical movements exceeding 3 mm are generally unpreferable since they cause unexpectedly large vertical amplitude. When the discharge spout 26 is lifted from the hydrophobic solvent 12, the distance of the discharge spout from the liquid surface is not particularly limited. However, it is preferably 1-5 mm. When the distance from the liquid level is less than 1 mm, lifting may not be ensured. Since unnecessarily large vertical amplitude is not preferable, the lift distance is preferably less than 5 mm. When the hydrophobic solvent 12 is stirred using an agitation blade 13, mutual adhesion of the formed aqueous gelatin solution droplets 14 can be suppressed.

Generally, the temperature of the hydrophobic solvent that receives the aqueous gelatin solution discharged from the nozzle needs to be maintained at not less than 20° C., which is the gelling temperature of gelatin. When the temperature of the hydrophobic solvent is lower than the gelling temperature of gelatin, the aqueous gelatin solution is gelled at the nozzle tip to problematically cause clogging of the nozzle. As a result, the aqueous gelatin solution cannot be discharged in a given quantity, and the particle size may vary for lack of smooth disengagement of the aqueous gelatin solution from the nozzle tip. In one embodiment of the present invention, therefore, the nozzle temperature controller (not shown) is installed to heat the nozzle tip including the discharge spout. By heating the nozzle tip to not lower than the gelling temperature of the aqueous gelatin solution in this way, even when the temperature of the hydrophobic solvent is lower than the gelling temperature, gelling of the aqueous gelatin solution at the nozzle tip can be suppressed and clogging of nozzle and variation of the particle size of gelatin particles can be avoided.

On the other hand, when the temperature of the hydrophobic solvent is not higher than the gelling temperature of gelatin, the aqueous gelatin solution solidifies to prevent mutual adhesion of gelatin particles. As in one embodiment of the present invention, therefore, superior effects of prevention of clogging of nozzle and variation of the particle size of gelatin particles, as well as simultaneous prevention of mutual adhesion of gelatin particles can be obtained by maintaining the temperature of the hydrophobic solvent at not higher than the gelling temperature, and heating the nozzle tip to not lower than the gelling temperature of the aqueous gelatin solution. In other words, the production method of the present invention can simplify the production steps of gelatin particles as well as produce particles having a desired particle size in a high yield.

The kind of the gelatin to which the production method of the present invention can be applied is not particularly limited. For example, gelatin particles derived from cattle bones, cattle skin, pig bone, pig skin and the like can be produced.

The concentration of the aqueous gelatin solution is preferably 2 wt %-20 wt %, particularly preferably 5 wt %-15 wt %. When the aqueous solution has a concentration of less than 2 wt %, spherical particles cannot be produced easily, and when it has a concentration of more than 20 wt %, the aqueous solution becomes highly viscous, making discharge difficult.

The shape of the gelatin particles is preferably as spherical as possible rather than amorphous. When the gelatin particles are injected into the blood vessel, spherical particles can embolize the blood vessel at a position as close as possible to the target site and can also reduce the pain to the patient.

To embolize blood vessels at positions as close as possible to the target site and select particles appropriate for the size of the blood vessels to avoid an adverse influence on the healthy part, suitable particle size of the gelatin particles includes three ranges of 40-100 µm, 150-300 µm and 400-800 µm. A small particle size of less than 40 µm is not preferable since such particles embolize blood vessels other than those in the object part. The production method of the present invention can conveniently produce gelatin particles having the above-mentioned three ranges of particle size, and also realize sharp particle size distribution where all particles show ±25% of the object central particle size of each of the above three particle size ranges.

The particle size of gelatin particles produced by the production method of the present invention can be controlled by adjusting the pressure of the pressurized air (i.e., discharge pressure), displacement of piston-needle, nozzle shape, bore of discharge spout of nozzle, vertical amplitude, discharge time and the like. Even when the nozzle shape and the bore of discharge spout of nozzle are the same, the size of the gelatin particles can be controlled by controlling the speed of the vertical movement of the nozzle (i.e., number of up-and-down motion per min) and the discharge pressure. As shown in FIG. 3B, a piston-needle 28 is a cylindrical piston movable in the up and down direction and formed in the center of a liquid discharge mechanism 30. When piston-needle 28 moves upward, a predetermined amount of the aqueous gelatin solution 11 supplied from liquid feed port 29 is uptaken into a cylindrical body surrounding the piston-needle 28, and when the piston-needle 28 moves downward, a predetermined amount of the aqueous gelatin solution 11 uptaken thereinto is discharged from the discharge spout 26. In this case, the pressure for discharging the aqueous gelatin solution from the nozzle tip into the hydrophobic solvent is preferably not less than 0.001 MPa. When it is less than 0.001 MPa, discharge of the aqueous gelatin solution from the nozzle is difficult.

An optimal range of the discharge rate of the aqueous gelatin solution depends on the particle size of desired gelatin particles and the concentration of the aqueous gelatin solution. For example, when 50 µm particles are to be obtained using 5 wt % aqueous gelatin solution, the discharge rate of about 0.001 ml is suitable. When 200 µm particles and 500 µm particles are to be obtained, the discharge rate is about 0.08 ml and about 1.30 ml, respectively.

Figure 4:
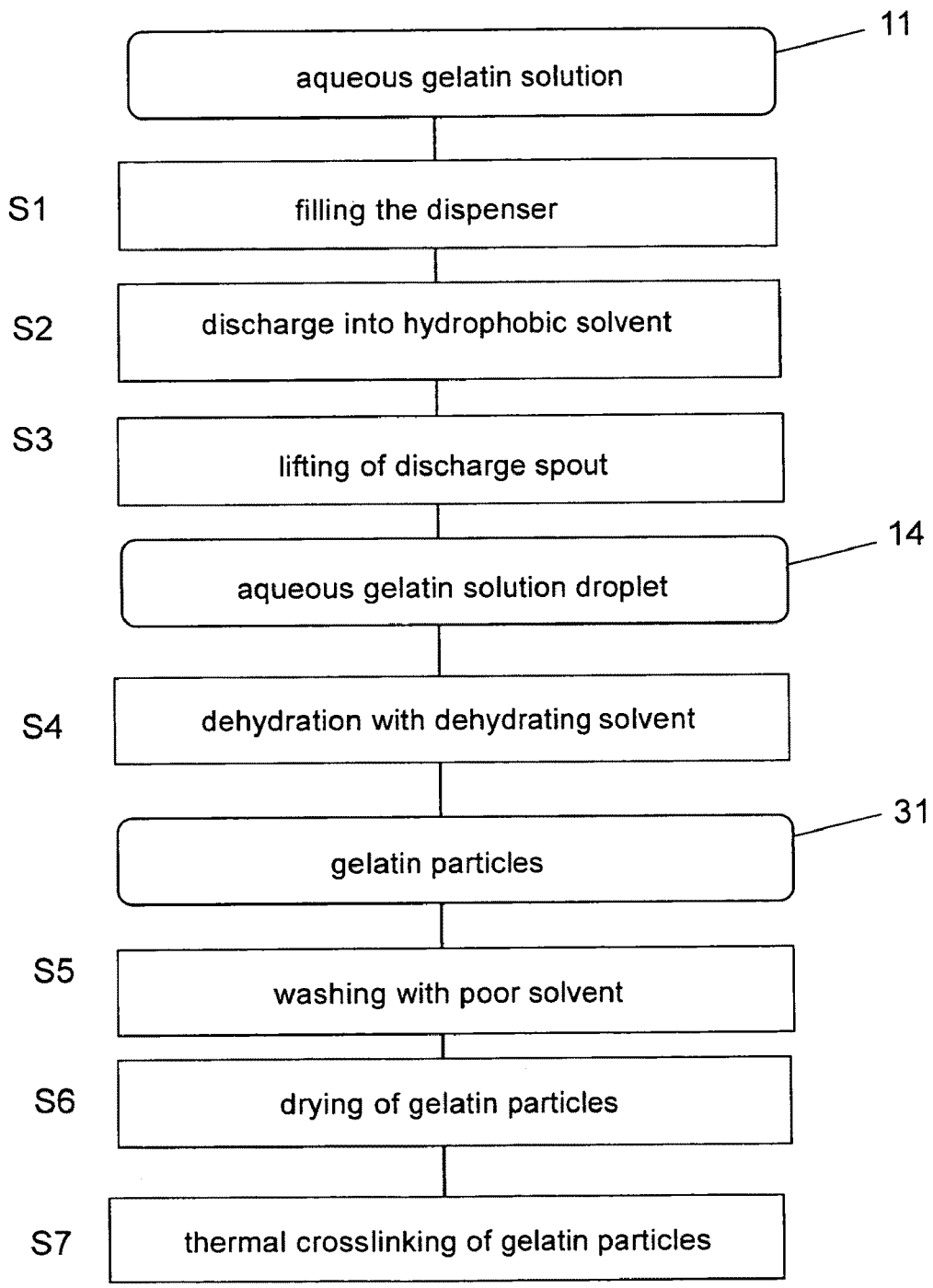
FIG. 4 is a flowchart explaining the production method of one embodiment of the present invention.

Next, one embodiment of the present invention is concretely explained by each step following the flowchart of FIG. 4.

In the production method of the gelatin particles in one embodiment of the present invention, the aqueous gelatin solution 11 is prepared as follows. First, gelatin is swollen in water at about 0° C., and stirred in warm water at about 40° C.-60° C. using a stirrer, an agitating blade, a shaker and the like for about 0.5 hr-about 1.5 hr to completely dissolve gelatin. Getalin can be completely dissolved in a short time by these procedures.

In step S1 for supply of the aqueous gelatin solution to a dispensing body 23, a container 20, a piping 21 and the body of a dispenser 23 are preferably heated to about 40° C.-60° C. Heating here can prevent gelling in the apparatus, thus enabling stable discharge of the aqueous gelatin solution.

In the next step S2 for discharge of the aqueous gelatin solution 11 into the hydrophobic solvent 12, the nozzle 24 is preferably heated to about 40° C.-60° C. Heating here can prevent gelling of the aqueous gelatin solution 11, thus enabling discharge of a given amount of the aqueous gelatin solution continuously and for a long time.

In step S3 for lifting of the discharge spout 26, the discharge spout 26 immersed in the hydrophobic solvent 12 is lifted from the hydrophobic solvent 12. In the discharge step, the discharged aqueous gelatin solution is attached to the tip of the discharge spout 26. When the discharge spout 26 with the aqueous gelatin solution attached thereto is lifted, the aqueous gelatin solution attached to the discharge spout 26 passes through the interface between the hydrophobic solvent 12 and air. As a result, the aqueous gelatin solution detaches therefrom and drops into the hydrophobic solvent 12 to form the aqueous gelatin solution droplet 14. Thereafter, the discharge spout 26 moves downward and performs the next cycle of discharge.

The temperature of the hydrophobic solvent 12 is preferably 0° C.-60° C. Particularly, the temperature is more preferably not higher than the gelling temperature of the aqueous gelatin solution 11. By setting the temperature of the hydrophobic solvent 12 to not higher than the gelling temperature, the droplet 14 of the aqueous gelatin solution is solidified earlier, collision of particles, and deformation or separation of particles due to the shear force during stirring of the solvent can be suppressed. In addition, mutual adhesion and coagulation of the droplets 14 of the aqueous gelatin solution can also be prevented. The hydrophobic solvent may be any as long as it is pharmaceutically acceptable and, for example, vegetable oil such as olive oil and the like, fatty acid such as oleic acid and the like, fatty acid ester such as caprylic triglyceride and the like, hydrocarbon solvents such as hexane and the like, animal oil, mineral oil, silicone oil and the like can be used. Of these, olive oil and caprylic triglyceride which is chain fatty acid ester which resists oxidation are preferable.

In step S4 for dehydration of water in the aqueous gelatin solution droplet 14, a dehydrating solvent at a temperature of not higher than the gelling temperature is added to remove water in the droplets 14 of the aqueous gelatin solution so that the aqueous gelatin solution droplet 14 will not be dissolved. Thus, the dehydrating solvent is preferably contacted with the aqueous gelatin solution droplet 14 for about 15 min or longer. The temperature of the dehydrating solvent is particularly preferably not higher than the gelling temperature of the gelatin. By dehydrating water in the aqueous gelatin solution droplet 14 in this way, coagulation of the formed gelatin particles 31 can be prevented and uniform crosslinking in a later step becomes possible. As the dehydrating solvent, for example, ketone solvents such as acetone and the like, alcoholic solvent such as isopropyl alcohol and the like, ester solvents such as ethyl acetate and the like, hydrocarbon solvents such as toluene, hexane and the like, halogenated solvents such as dichloroethane and the like can be used.

In step S5 for washing gelatin particles 31, gelatin particles 31 are washed with a poor solvent in which the gelatin particles 31 are not dissolved. The poor solvent is preferably used at a temperature not higher than the gelling temperature of the gelatin. By washing according to a method such as sieving, centrifugation and the like, gelatin particles 31 and the poor solvent can be separated. As the poor solvent in which the aqueous gelatin solution droplet is not dissolved, for example, ketone solvents such as acetone and the like, alcoholic solvents such as isopropyl alcohol and the like, ester solvents such as ethyl acetate and the like, hydrocarbon solvents such as toluene, hexane and the like, and halogenated solvents such as dichloroethane and the like can be used. In the washing step S5, washing about 2-15 g of gelatin particles 31 for 15-30 min using about 200-300 ml of a solvent is one cycle and this cycle is preferably repeated 4-6 times. Using agitating blade, shaker, ultrasonic washing machine and the like, washing can be conducted more effectively.

In step S6 for drying gelatin particles 31, the washing solvent attached to gelatin and water in the gelatin particles 31 are removed at a temperature at which the gelatin particles 31 are not dissolved, and various methods such as ventilation drying, drying under reduced pressure, freeze-drying and the like can be employed. For example, drying at 5° C.-25° C. for about 12 hr or longer is preferable, and drying under reduced pressure is particularly preferable.

In step S7 for crosslinking gelatin particles 31, gelatin particles 31 are heated at 80° C.-250° C. for 0.5 hr-120 hr. The heating conditions are determined according to the time necessary for completely decomposing gelatin particles in the blood vessels; in other words, the time from embolization of the blood vessels with gelatin particles 31 up to re-opening of the blood flow. In addition, the heating time depends on the heating temperature. For necrosis of tumor (cancer), 2-3 days of embolization of the blood vessel is generally required. Therefore, for example, when the decomposition period of the gelatin particles 31 is set to 3-7 days, the conditions of thermal crosslinking are preferably heating at 100° C.-180° C. for not less than 1 hr and not longer than 24 hr. To avoid inconveniences such as oxidization of gelatin particles 31 and the like, the crosslinking step S7 is preferably performed under reduced pressure or inert gas atmosphere.

The production method of the present embodiment is particularly suitable for the production of non-porous gelatin particles. When porous gelatin particles are used, gelatin particles may be partly separated to form fine particles during decomposition in the blood vessels, and such fine particles may be transported by the blood flow to embolize blood vessels other than the object part. In contrast, non-porous gelatin particles are gradually dissolved from the outer circumference of the gelatin particles. Therefore, the possibility of developing such fine particles is advantageously low.

EXAMPLES

The present invention is explained in more detail in the following by referring to Examples, which are not to be construed as limitative.

Example 1

Olive oil (about 100 ml) was added to a solvent bath, and a discharge spout of the dispenser was set such that it was immersed by about 1 mm in the olive oil. Gelatin (2 g) was swollen in advance in cold water (about 18 ml) for 30 min, and the swollen gelatin was dissolved in warm water at 40-50° C. while heating for about 1 hr to give an aqueous gelatin solution. The prepared aqueous gelatin solution was defoamed and filled in the body of a dispenser (741MD-SS, manufactured by SAN-EI TECH Ltd.). The body was pressurized with 0.01 MPa pressurized air, and the aqueous gelatin solution was discharged from a polypropylene needle nozzle (inner diameter 0.10 mm, GP needle nozzle 32G, manufactured by SAN-EI TECH Ltd.) into the olive oil while vibrating the needle nozzle at an up and down amplitude of about 3 mm across the surface of the olive oil. In this case, the aqueous gelatin solution was discharged in a given quantity from the discharge spout immersed in the olive oil and, when the discharge spout was lifted from the olive oil, the discharged aqueous gelatin solution was disengaged from the discharge spout and dispersed in the olive oil. The discharge spout once lifted was immersed in the olive oil again for the next discharge action. These series of steps (immersion-discharging-lifting) were performed at a rate of 400 times/min in Example 1. During these steps, the olive oil was stirred. By stirring the olive oil, the droplets of the discharged aqueous gelatin solution could be dispersed by each droplet without forming sediments in the olive oil. Then, the olive oil was cooled from the circumference with cold water, whereby the aqueous gelatin solution droplets formed in the olive oil were solidified by cooling. Thereafter, ice-cooled acetone was added to the olive oil to dehydrate the droplets of the aqueous gelatin solution, whereby gelatin particles were obtained. The obtained gelatin particles were removed and washed with ice-cooled acetone to give gelatin particles without residual olive oil. Then, the gelatin particles were dried in vacuo for 12-24 hr, and sequentially subjected to thermal crosslinking under reduced pressure at 140° C. for 24 hr to give water insoluble gelatin particles.

Example 2

Using apparatuses and conditions similar to those in Example 1 except that the inside of the body was pressurized with 0.30 MPa pressurized air and polypropylene needle nozzle (inner diameter 0.20 mm) was used, water insoluble gelatin particles were prepared.

Comparative Example 1

Olive oil (about 700 ml) was added to a 1000 ml upright flask, and an agitating blade was set. Gelatin (2 g) was swollen in advance in cold water (18 ml) for 30 min, and the swollen gelatin was dissolved in warm water at 40-50° C. while heating for about 1 hr to give an aqueous gelatin solution. The agitating blade was rotated at 200 rpm to stir the olive oil, during which 20 g of the aqueous gelatin solution was added using a dropping funnel. The mixture was successively stirred for about 10-30 min to give aqueous gelatin solution droplets. Then, the olive oil was cooled from the circumference with cold water, whereby the aqueous gelatin solution droplets formed in the olive oil were solidified by cooling. Thereafter, ice-cooled acetone was added to the olive oil to dehydrate the droplets of the aqueous gelatin solution, whereby gelatin particles were obtained. The obtained gelatin particles were removed and washed with ice-cooled acetone to give gelatin particles without residual olive oil. Then, the gelatin particles were dried in vacuo for 12-24 hr, and sequentially subjected to thermal crosslinking under reduced pressure at 140° C. for 24 hr to give water insoluble gelatin particles.

Comparative Example 2

Olive oil (700 ml) was added to a 1000 ml upright flask and an agitating blade was set. Gelatin (about 2 g) was swollen in advance in cold water (11 ml) for 30 min, and the swollen gelatin was dissolved in warm water at 40-50° C. while heating for about 1 hr to give an aqueous gelatin solution. The agitating blade was rotated at 100 rpm to stir the olive oil, during which 13 g of the aqueous gelatin solution was added using a dropping funnel. The mixture was successively stirred for about 10-30 min to give aqueous gelatin solution droplets. Hereafter Comparative Example 1 was followed to give water insoluble gelatin particles.

The measurement results and evaluation results of the water insoluble gelatin particles obtained in Examples 1 and 2 and Comparative Examples 1 and 2 are explained in the following.

(Particle Shape)

Figure 5A:
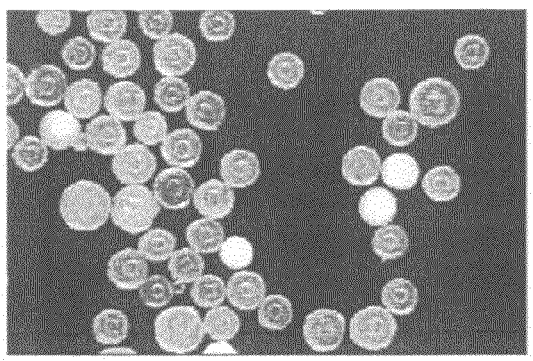
FIGS. 5A-5D show particle shapes of the gelatin particles.
Figure 5B:
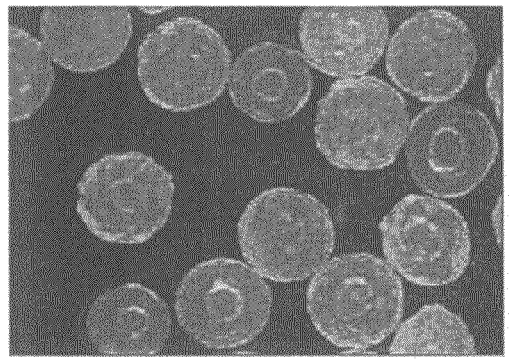
Figure 5C:
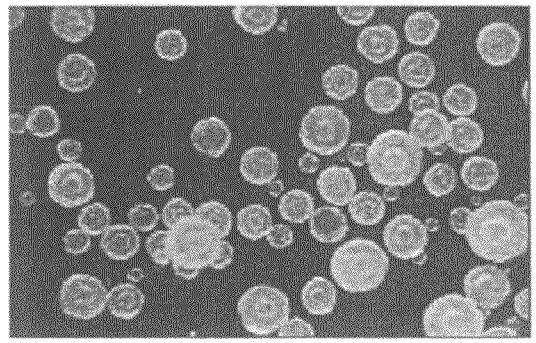
Figure 5D:
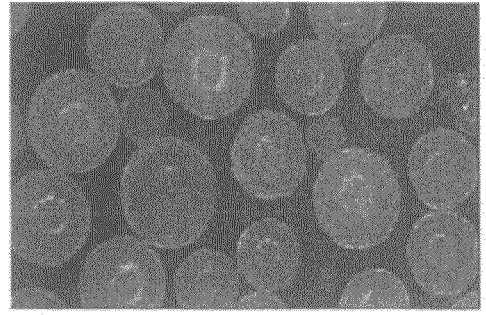

The water insoluble gelatin particles obtained in Examples 1 and 2 and Comparative Examples 1 and 2 were observed under a microscope with 100-fold magnification and the results are shown in FIGS. 5A-D. FIG. 5A shows the particle shape of the gelatin particles prepared by the method of Example 1, FIG. 5B shows the particle shape of the gelatin particles prepared by the method of Example 2, FIG. 5C shows the particle shape of the gelatin particles prepared by the method of Comparative Example 1, and FIG. 5D shows the particle shape of the gelatin particles prepared by the method of Comparative Example 2. From FIG. 5, it was confirmed that all gelatin particles were about spherical.

(Particle Size Distribution)

Figure 6:
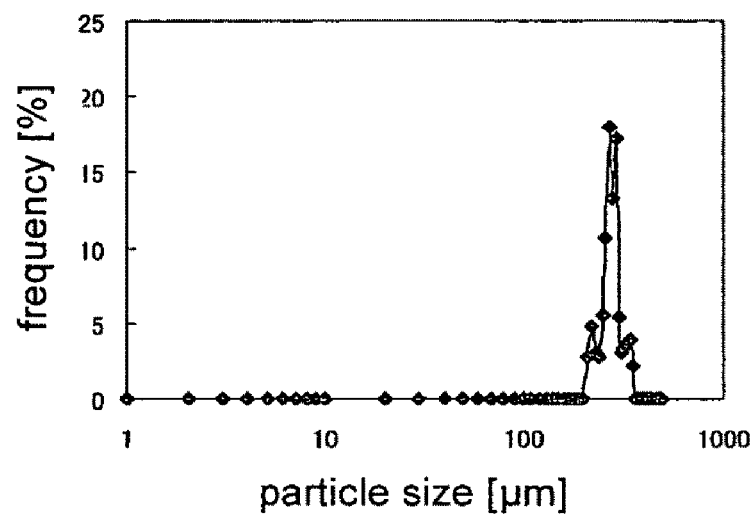
FIG. 6 shows particle size distribution of the gelatin particles prepared in Example 1.
Figure 7:
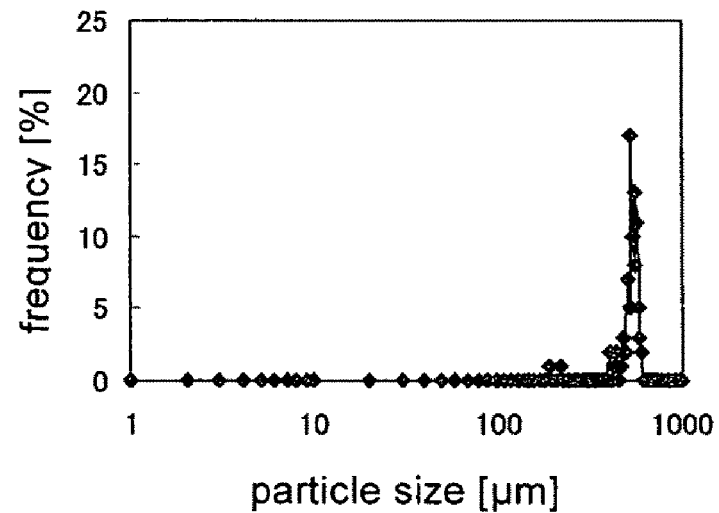
FIG. 7 shows particle size distribution of the gelatin particles prepared in Example 2.
Figure 8:
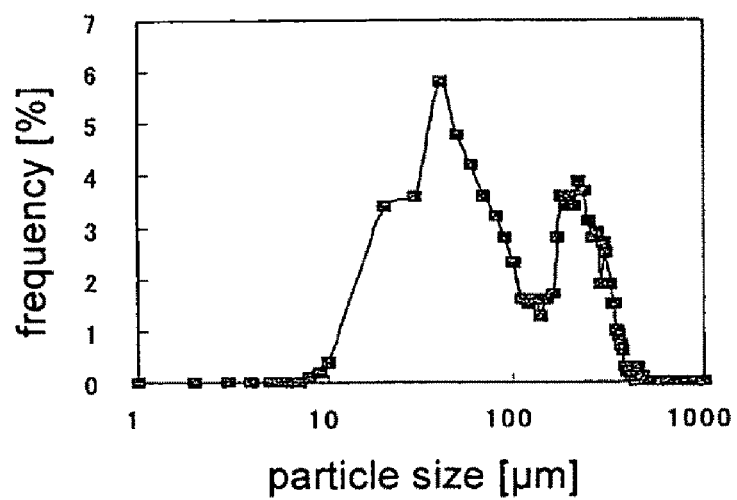
FIG. 8 shows particle size distribution of the gelatin particles prepared in Comparative Example 1.
Figure 9:
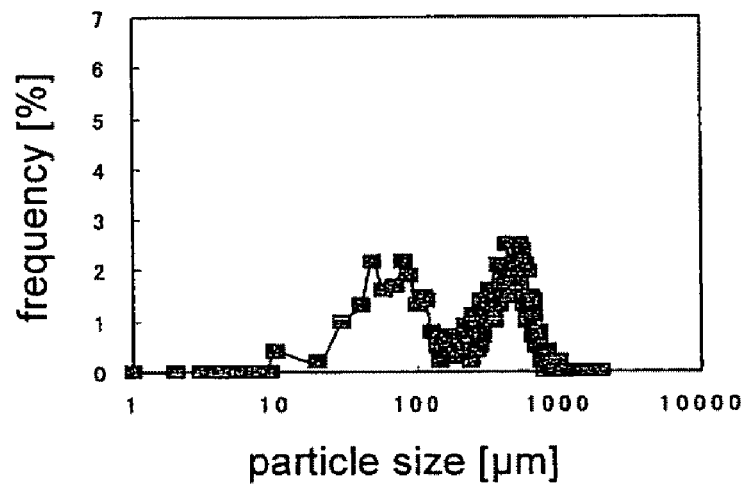
FIG. 9 shows particle size distribution of the gelatin particles prepared in Comparative Example 2.

The particle size of the gelatin particles obtained in Examples 1 and 2 and Comparative Examples 1 and 2 was measured for 100 particles for each Example under a microscope. The particle size distribution is shown in FIG. 6-FIG. 9. FIGS. 6, 7, 8 and 9 correspond to Example 1, Example 2, Comparative Example 1 and Comparative Example 2, respectively. The horizontal axis in the Figures shows particle size, and the vertical axis shows frequency (%) of the particles having the corresponding particle size. For example, a frequency of 6% in 50 μm particle size means that 6 particles in 100 particles have a particle size of 50 μm. As shown in FIGS. 8 and 9, in the particles obtained in Comparative Examples 1 and 2, the range of the particle size was wide and from a few μm to several thousand μm. On the other hand, as shown in FIGS. 6 and 7, the particles obtained in Examples 1 and 2 showed extremely sharp particle size distribution.

(Particle Yield)

The gelatin particles obtained in Examples 1 and 2 and Comparative Examples 1 and 2 were classified using sieves with apertures 600, 425, 250, 150, 106 and 53 μm, and the yield was calculated by measuring the weight of the particles with the object particle size and remaining on the sieves. The results are shown in Table 1.

TABLE 1

|  | object particle size | yield |
| --- | --- | --- |
| Example 1 | 150-200 μm | 86% |
| Example 2 | 425-500 μm | 90% |
| Comparative Example 1 | 150-200 μm | 38% |
| Comparative Example 2 | 425-500 μm | 30% |

From the results of Table 1, in Comparative Examples 1 and 2, the gelatin particles in the object particle size range showed a low yield of not more than 40% of the whole particles. In contrast, in Example 1, 86% of the whole particles showed a narrow range of 150 μm-200 μm, even in the particles having a small diameter of 150-200 μm. In addition, in about 500 μm particles, 90% of the whole particles showed a narrow range of 425 μm-500 μm, and further showed sharp particle size distribution characteristics.

This application is based on a patent application No. 2008-246417 filed in Japan, the contents of which are incorporated in full herein by this reference.

(Reference Numerals)
11 aqueous gelatin solution
12 hydrophobic solvent
13 agitating blade
14 aqueous gelatin solution droplet
15 cooling water
16 solvent bath
20 container for preparation of aqueous gelatin solution
21 piping
22 pressurized air
23 dispensing body
24 nozzle
25 needle
26 discharge spout
27 dispenser controller
28 piston-needle
29 liquid feed port
30 liquid discharge mechanism
31 gelatin particles

The invention claimed is:

1. A method of producing gelatin particles, comprising immersing a discharge spout on a nozzle tip of a dispenser in a hydrophobic solvent, discharging a predetermined amount of an aqueous gelatin solution from said discharge spout into the hydrophobic solvent, lifting, subsequent to discharging, the discharge spout from the hydrophobic solvent, dehydrating water in the droplets of the aqueous gelatin solution formed in the hydrophobic solvent using a dehydrating solvent, washing the dehydrated gelatin particles with a poor solvent of the gelatin particles, drying the collected gelatin particles, and thermally crosslinking the dried gelatin particles, wherein the droplets of the aqueous gelatin solution formed at the discharge spout during discharging are disengaged from the discharge spout during lifting; and the dehydrating solvent and the poor solvent are each at least one kind selected from the group consisting of acetone, isopropyl alcohol, ethanol, methanol, toluene, ethyl acetate, hexane and an organic halogen solvent.

2. The production method of claim 1, wherein the discharging step comprises discharging an aqueous gelatin solution contained in a dispensing body from the discharge spout into the hydrophobic solvent by air pressure, and the particle size of the gelatin particles can be controlled by air pressure, piston-needle displacement, discharge time, or diameter of the nozzle discharge spout.

3. The production method of claim 1, wherein the discharge spout is immersed by 0.2 mm-3 mm in the hydrophobic solvent in the discharging step.

4. The production method of claim 1, wherein, in the discharging step, the vertical amplitude of the nozzle motion is 1-5 mm and the number of up-and-down motion is 1000 cycles or below per minute.

5. The production method of claim 1, wherein the hydrophobic solvent is stirred.

6. The production method of claim 1, wherein, in the discharging step, the aqueous gelatin solution is discharged from the discharge spout into the hydrophobic solvent with a pressure of not less than 0.001 MPa.

7. The production method of claim 1, wherein the concentration of the aqueous gelatin solution is 2 wt %-20 wt %.

8. The production method of claim 1, wherein the discharging step is performed using a container in which the aqueous gelatin solution is prepared, a piping for transporting the aqueous gelatin solution from the container to the dispensing body, a dispenser with a nozzle for discharging the aqueous gelatin solution into the hydrophobic solvent, and a bath for storing the hydrophobic solvent, and each apparatus can be temperature-controlled to maintain the temperature of the aqueous gelatin solution.

9. The production method of claim 1, wherein the hydrophobic solvent is at least one kind selected from the group consisting of animal oil, vegetable oil, mineral oil, silicone oil, fatty acid, fatty acid ester and an organic solvent.

10. The production method of claim 1, wherein the gelatin particles are washed by at least one method selected from the group consisting of sieving and centrifugation.

11. The production method of claim 1, wherein the dehydrated gelatin particles are dried by at least one method selected from the group consisting of ventilation drying, drying under reduced pressure and freeze-drying.

12. The production method of claim 1, wherein, in the thermal crosslinking step, the heating temperature is 80° C.-250° C., and the heating time is 0.5 hr-120 hr.

13. The production method of claim 1, wherein the gelatin particles have a spherical shape.

14. The production method of claim 1, wherein the gelatin particles after thermal crosslinking have a particle size of not more than 2000 μm.

15. The production method of claim 1, wherein, in the discharging step, the tip of the nozzle is heated to 20° C. or above, and the hydrophobic solvent is controllable to 0° C.-60° C.

16. The production method of claim 1, wherein a plurality of droplets of the aqueous gelatin solution are produced by alternately repeating the discharging step and the lifting step plural times.

* * * * *